United States Patent
Liu

(10) Patent No.: US 9,623,592 B2
(45) Date of Patent: Apr. 18, 2017

(54) THERMOPLASTIC ELASTOMER COMPOSITE, ELECTRONIC CIGARETTE COMPONENT AND METHOD FOR PRODUCING THE SAME

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 737 days.

(21) Appl. No.: 13/962,706

(22) Filed: Aug. 8, 2013

(65) Prior Publication Data

US 2014/0353867 A1 Dec. 4, 2014

Related U.S. Application Data

(63) Continuation of application No. PCT/CN2013/076324, filed on May 28, 2013.

(51) Int. Cl.

| | |
|---|---|
| B29C 45/00 | (2006.01) |
| C08K 3/22 | (2006.01) |
| B29C 45/78 | (2006.01) |
| B29C 45/74 | (2006.01) |
| B29C 45/57 | (2006.01) |
| B29C 45/73 | (2006.01) |
| B29C 45/77 | (2006.01) |
| C08J 9/00 | (2006.01) |
| C08J 9/32 | (2006.01) |
| C08L 75/00 | (2006.01) |
| C08L 75/04 | (2006.01) |
| A24F 47/00 | (2006.01) |
| A61M 15/06 | (2006.01) |
| C08K 5/14 | (2006.01) |
| C08K 5/3437 | (2006.01) |
| C08K 9/10 | (2006.01) |

(52) U.S. Cl.
CPC ...... *B29C 45/0001* (2013.01); *B29C 45/0013* (2013.01); *B29C 45/57* (2013.01); *B29C 45/73* (2013.01); *B29C 45/74* (2013.01); *B29C 45/77* (2013.01); *B29C 45/78* (2013.01); *C08J 9/0023* (2013.01); *C08J 9/0061* (2013.01); *C08J 9/0066* (2013.01); *C08J 9/32* (2013.01); *C08K 3/22* (2013.01); *C08L 75/00* (2013.01); *C08L 75/04* (2013.01); *A24F 47/008* (2013.01); *A61M 15/06* (2013.01); *C08J 2201/026* (2013.01); *C08J 2203/22* (2013.01); *C08J 2207/00* (2013.01); *C08J 2300/22* (2013.01); *C08J 2300/26* (2013.01); *C08J 2375/04* (2013.01); *C08J 2423/08* (2013.01); *C08J 2423/28* (2013.01); *C08J 2431/04* (2013.01); *C08J 2453/00* (2013.01); *C08K 5/14* (2013.01); *C08K 5/3437* (2013.01); *C08K 9/10* (2013.01)

(58) Field of Classification Search
CPC . B29C 45/0001; B29C 45/0013; B29C 45/57; B29C 45/73; B29C 45/74; B29C 45/77; B29C 45/78
USPC ................................. 264/51, 328.16, 328.18
See application file for complete search history.

(56) References Cited

U.S. PATENT DOCUMENTS

| | | | | |
|---|---|---|---|---|
| 2,371,868 | A * | 3/1945 | Berg | B41N 7/06 101/335 |
| 6,184,259 | B1 * | 2/2001 | Peretti | A43B 13/04 264/45.4 |
| 8,998,609 | B2 * | 4/2015 | Prakash | A61B 1/0005 433/214 |
| 9,185,937 | B2 * | 11/2015 | Liu | A24F 47/008 |
| 2007/0069412 | A1 * | 3/2007 | Whinnery, Jr. | C08G 18/092 264/51 |
| 2009/0118040 | A1 * | 5/2009 | De Garavilla | C08K 5/09 473/373 |
| 2010/0273905 | A1 * | 10/2010 | Muenz | C08L 63/00 521/135 |
| 2010/0304893 | A1 * | 12/2010 | De Garavilla | A63B 37/0003 473/373 |
| 2013/0029069 | A1 * | 1/2013 | Soddemann | C08L 9/02 428/35.7 |
| 2013/0209954 | A1 * | 8/2013 | Prakash | A61B 1/00188 433/29 |
| 2014/0196733 | A1 * | 7/2014 | Liu | A24F 47/008 131/329 |

FOREIGN PATENT DOCUMENTS

| | | | |
|---|---|---|---|
| CN | 102010533 A | * | 4/2011 |
| CN | 102250408 A | * | 11/2011 |

* cited by examiner

*Primary Examiner* — Atul P. Khare
(74) *Attorney, Agent, or Firm* — Tim Tingkang Xia, Esq.; Locke Lord LLP

(57) ABSTRACT

The invention discloses a thermoplastic elastomer composite, a component of electronic cigarette and a method of preparing the component of electronic cigarette. The thermoplastic elastomer composite comprises 65-85 weight % of a main body material, 10-25 weight % of a microspheres foaming agent and 5-10 weight % of an agent. The component of electronic cigarette made of the thermoplastic elastomer composite, has high elasticity and a wide hardness adjusting range, can be adjusted according to users' requirements, and has good taste and feel. The component can be provided with decorative patterns that are similar to tobacco leaves in production, and can simulate appearance of a real cigar and visual effects of real tobacco of cigarettes. The component has high elasticity, and it is non-toxic and non-pollution. The method can be carried out in a simple manner, and can improve the production efficiency.

2 Claims, 1 Drawing Sheet

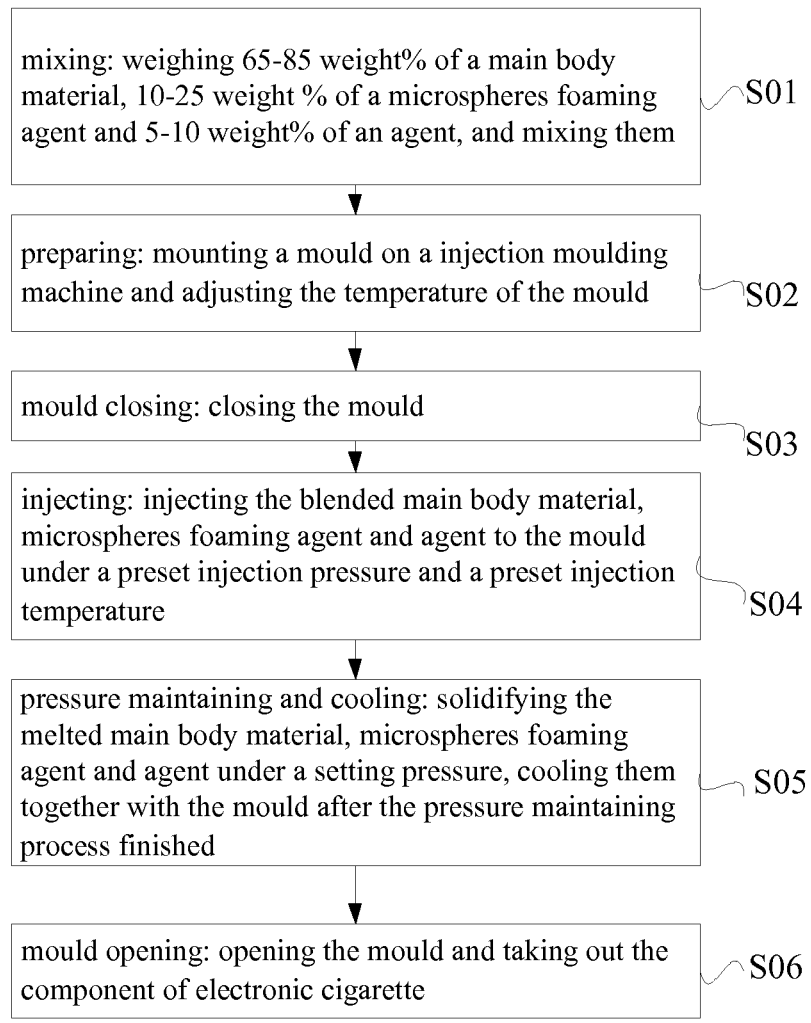

THERMOPLASTIC ELASTOMER COMPOSITE, ELECTRONIC CIGARETTE COMPONENT AND METHOD FOR PRODUCING THE SAME

CROSS-REFERENCE TO RELATED APPLICATIONS

This application is a continuation of International Patent Application No. PCT/CN2013/076324, with an international filing date of May 28, 2013, designating the United States, now pending. The contents of these specifications are incorporated herein by reference.

FIELD OF THE INVENTION

The present invention relates to the technical field of electronic cigarettes, and more particularly, relates to a thermoplastic elastomer composite, an electronic cigarette component and a method for producing the electronic cigarette component.

BACKGROUND OF THE UTILITY MODEL

Because domestic publicity of anti-smoking and the people's awareness of health are enhanced, electronic cigarettes, which serve as the substitute of traditional tobacco, have been more and more widely used. An existing electronic cigarette comprises a cigarette rod and a cigarette holder fixed together. A battery is received in the cigarette rod, and an atomizer is received in the cigarette holder. The cigarette rod and the atomizer are in electronic connection with each other. An oil cup is mounted in the cigarette rod to contain tobacco juice. When a user uses an electronic cigarette for smoking, the user suctions the cigarette holder. Thus, the tobacco juice flows into the atomizer slowly. An atomizing wire of the atomizer absorbs the tobacco juice. A current signal is sensed by a control circuit board of the cigarette rod and the control circuit board controls a heating device near the atomizing wire to atomize the tobacco juice. Finally, a tobacco smog is generated and is inhaled by the user via a suction nozzle cover.

Since the suction nozzle cover contacts the mouth of the user directly, material of the suction nozzle cover should meet high requirement. Existing suction nozzle cover are all made of plastic or silica gel, and the like, which may have bad elasticity and bad taste, and may be difficult to achieve appearance of a real cigar. Thus, user experience may be adversely affected.

SUMMARY OF THE INVENTION

Aiming at the drawbacks in the prior art that the suction nozzle cover makes a bad taste for users, a thermoplastic elastomer composite, a component of electronic cigarette and a method for producing the component of electronic cigarette are provided in the present invention. In the present invention, the suction nozzle cover is made of the thermoplastic elastomer composite. The suction nozzle cover has high elasticity and is provided with a decorative pattern of tobacco leaf, which will enhance the user experience.

A thermoplastic elastomer composite according to the present invention comprises 65-85 weight % of a main body material, 10-25 weight % of a microspheres foaming agent and 5-10 weight % of an agent.

In the thermoplastic elastomer composite of the invention, the agent is any one of a toughener, an activating agent, a cross linking agent and a toner.

In the thermoplastic elastomer composite of the invention, the agent comprises: 30-40 weight % of the toughener, 10-20 weight % of the activating agent, 10-20 weight % of the cross linking agent and 30-40 weight % of the toner.

In the thermoplastic elastomer composite of the invention, the toughener is any one of a styrene-butadiene-styrene block copolymers, an ethylene-vinyl acetate copolymer and a chlorinated polyethylene.

In the thermoplastic elastomer composite of the invention, the activating agent is any one of a zinc oxide, a calcium oxide, a zinc carbonate and a stearic acid.

In the thermoplastic elastomer composite of the invention, the cross linking agent is any one of a dicumyl peroxide, a di-tert-butyl peroxide and a lauroyl peroxide.

In the thermoplastic elastomer composite of the invention, the main body material is any one of a thermoplastic polyurethanes, a thermoplastic elastomer, and a thermoplastic rubber.

An electronic cigarette component according to the invention, the component is made of a thermoplastic elastomer composite.

In the electronic cigarette component of the invention, the component is at least one of a suction nozzle cover, a protecting sleeve, a crown top and a suction nozzle.

A method for producing the electronic cigarette component of the present invention comprises the following steps:

mixing: weighing 65-85 weight % of a main body material, 10-25 weight % of a microspheres foaming agent and 5-10 weight % of an agent, and mixing the main body material, the microspheres foaming agent and the agent together;

preparing: mounting a mould on a injection moulding machine and adjusting the temperature of the mould;

mould closing: closing the mould;

injecting: injecting the blended main body material, microspheres foaming agent and agent into the mould under a preset injection pressure and a preset injection temperature;

pressure maintaining and cooling: solidifying the melted main body material, microspheres foaming agent and agent under a setting pressure, cooling solidified main body material, microspheres foaming agent and agent together with the mould after the pressure maintaining process finished;

mould opening: opening the mould and taking out the component of electronic cigarette.

In the method for producing the electronic cigarette component of the invention, the temperature of the mould is ranged from 40° C. to 50° C.

In the method for producing the electronic cigarette component of the invention, the preset injection pressure is ranged from 40 Mpa to 60 Mpa, and the preset injection temperature is ranged from 160° C. to 200° C.

In the method for producing the electronic cigarette component of the invention, a duration for cooling in the mould is range from 15 s to 20 s.

In the method for producing the electronic cigarette component of the invention, the main body material is any one of a thermoplastic polyurethanes, a thermoplastic elastomer, and a thermoplastic rubber.

In the method for producing the electronic cigarette component of the invention, the agent is any one of a toughener, an activating agent, a cross linking agent and toner.

In the method for producing the electronic cigarette component of the invention, the agent comprises: 30-40 weight % of the toughener, 10-20 weight % of the activating agent, 10-20 weight % of the cross linking agent and 30-40 weight % of the toner.

In the method for producing the electronic cigarette component of the invention, the toughener is any one of a styrene-butadiene-styrene block copolymers, an ethylene-vinyl acetate copolymer and a chlorinated polyethylene.

In the method for producing the electronic cigarette component of the invention, the activating agent is any one of a zinc oxide, a calcium oxide, a zinc carbonate and a stearic acid.

In the method for producing the electronic cigarette component of the invention, the cross linking agent is any one of a dicumyl peroxide, a di-tert-butyl peroxide and a lauroyl peroxide.

When implementing the invention, the following advantages can be achieved: the component of electronic cigarette made of the thermoplastic elastomer composite has high elasticity and a wide hardness adjusting range, can be adjusted according to users' requirements, and further has good taste and feel. The component can be provided with decorative patterns that are similar to tobacco leaves in production, and can simulate appearance of a real cigar and visual effects of real tobacco of cigarettes. The component has high elasticity, and it is non-toxic and non-pollution. The method can be carried out in a simple manner, and can improve the production efficiency.

BRIEF DESCRIPTION OF THE DRAWINGS

The present invention can be further illustrated by reading the example with references made to the accompanying drawings, in which:

The FIGURE is a flow chart of a method for producing the component of electronic cigarette according to a preferred embodiment of the present invention.

DETAILED DESCRIPTION OF THE PREFERRED EMBODIMENT

For recognizing the technique character, the object and the effect more clearly, the special implement of the invention is illustrated in detail with references to the accompanying drawings.

A thermoplastic elastomer composite according to an embodiment of the present invention comprises 65-85 weight % of a main body material, 10-25 weight % of a microspheres foaming agent and 5-10 weight % of an agent.

The main body material is a kind of polymer material that can exhibit rubber elasticity at a room temperature and can also be plasticized at a high temperature, and this polymer material has good properties, such as aging resistant and oil resistant. In particular, the main body material is any one of a thermoplastic polyurethanes, a thermoplastic elastomer, and a thermoplastic rubber or their combinations. Preferably, the main body material is thermoplastic elastomer (TPE).

A foaming agent of the invention is a microspheres foaming agent. The microspheres foaming agent is a kind of foaming agent with a core-shell structure. Wherein, the shell is made of thermoplastic acrylic resin polymer, and the core is globular plastic particle that is formed by alkane gas. Wherein, diameters of the cores of the microspheres foaming agent are ranged from 10 to 45 µm, and the volumes of the cores can expand quickly to reach dozens of times of the original volumes of the cores after heated, thereby achieving foaming effects.

The microspheres foaming agent can expand at a certain temperature and dissolves in the melt or mash of the thermoplastic elastomer, which can generate pores in the thermoplastic elastomer to get a product with high elastomer. On the other hand, when generating the pores, a part of reaction heat can also be removed from the thermoplastic elastomer, which prevents the thermoplastic elastomer from being scorched due to the high temperature in the pore.

The agent is at least one of a toughener, an activating agent, a cross linking agent and toner.

The agent includes 30-40 weight % of the toughener, 10-20 weight % of the activating agent, 10-20 weight % of the cross linking agent, and 30-40 weight % of the toner.

The toughener is an annexing agent that can reduce brittleness and improve shock resistance of the polymer material. In the invention, the toughener of the component of the electronic cigarette is a resin toughener. In particular, the toughener is at least one of a styrene-butadiene-styrene block copolymers, an ethylene-vinyl acetate copolymer, and a chlorinated polyethylene. The toughener is configured to improve toughness of a suction nozzle cover and make surface of the suction nozzle cover be smooth.

The activating agent is configured to control the sizes and structures of the pores. In the invention, the activating agent is at least one of a zinc oxide, a calcium oxide, a zinc carbonate, and a stearic acid.

The cross linking agent is configured to form chemical bonds between linear molecules and make the linear molecules connect together, so that the linear molecules are constructed with a net structure. In this way, the strength and elasticity of a rubber can be improved. In the invention, the cross linking agent is a peroxide cross linking agent. The cross linking agent is any one of a dicumyl peroxide, a di-tert-butyl peroxide, and a lauroyl peroxide.

The toner is configured to color the component of the electronic cigarette and thereby meet different users' requirements.

The thermoplastic elastomer composite that includes 65-85 weight % of a main body material, 10-25 weight % of a microspheres foaming agent and 5-10 weight % of an agent has a wide hardness adjusting range and high elasticity. Furthermore, the thermoplastic elastomer composite is non-toxic and non-pollution, and is an environmental product.

An electronic cigarette component is also provided by the invention. The component is made of the aforementioned thermoplastic elastomer composite. The component may be at least one of a suction nozzle cover, a protecting sleeve, a crown top, and a suction nozzle, or others that meet users' requirements.

As shown in the figure, a method for producing the electronic cigarette component according to a preferred embodiment of the invention comprises the following steps:

S01. mixing: weighing 65-85 weight % of the main body material, 10-25 weight % of the microspheres foaming agent and 5-10 weight % of the agent, and mixing these materials together.

Wherein, 65-85 weight % of the main body material, 10-25 weight % of the microspheres foaming agent and 5-10 weight % of the agent are weighed. Wherein, the main body material is any one of a thermoplastic polyurethanes, a thermoplastic elastomer, and a thermoplastic rubber or their combinations. The main body material, the microspheres foaming agent and the agent are mixed together at a room temperature for 30 minutes-50 minutes. The volume of all of the constituents of the mixture mixed together is 5 mm³-20 mm³.

Wherein, the agent may be at least one of a toughener, an activating agent, a cross linking agent, and a toner.

The agent may include 30-40 weight % of the toughener, 10-20 weight % of the activating agent, 10-20 weight % of the cross linking agent and 30-40 weight % of the toner.

S02. preparing: mounting a mould on an injection moulding machine and adjusting the temperature of the mould.

The mould is mounted on the injection moulding machine, and the temperature of the mould is adjusted to 40° C. -50° C.

S03. mould closing: closing the mould.

A mould closing device of the injection moulding machine controls the mould to be closed. At the same time, the injection moulding machine controls a vacuum pump to vacuumize a cavity until the mould closing step is finished.

S04. injecting: injecting the mixed main body material, microspheres foaming agent and agent into the mould under a preset injection pressure and a preset injection temperature.

The preset injection pressure is ranged from 40 Mpa to 60 Mpa. The preset injection temperature is ranged from 160° C. to 200° C. Under such injection pressure and injection temperature, the mixed main body material, microspheres foaming agent and agent are injected into the mould described as above step S03. Wherein, an injection speed is ranged from 20 cm³/s to 40 cm³/s.

S05. pressure maintaining and cooling: solidifying the melted main body material, microspheres foaming agent and agent under a preset pressure, and cooling the main body material, microspheres foaming agent and agent in the mould after the pressure maintaining process is finished.

The duration for the pressure maintaining process may be determined according to the size of the product and the characters of the material. Generally, the duration is ranged from 10 s to 150 s. After the pressure maintaining process is finished, the product is cooled inside the mould. The duration for cooling is ranged from 15 s to 20 s.

S06. mould opening: opening the mould and taking out the component of electronic cigarette.

The mould closing device of the injection moulding machine controls the moving mould to draw back. The mould is opened and the product is pushed out, so that the whole producing process is finished.

The method can be carried out in a simple manner, and can improve the production efficiency. The component of electronic cigarette made of the thermoplastic elastomer composite has high elasticity and a wide hardness adjusting range, can be adjusted according to users' requirements, and further has good taste and feel. The component can be provided with decorative patterns that are similar to tobacco leaves in production, and can simulate appearance of a real cigar and visual effects of real tobacco of cigarettes. The component has high elasticity, and it is non-toxic and non-pollution.

EXAMPLE 1

A thermoplastic elastomer composite includes 65 weight % of the thermoplastic elastomer, 25 weight % of the microspheres foaming agent and 10 weight % of the agent. Wherein, the agent includes 30 weight % of styrene-butadiene-styrene block copolymers, 10 weight % of the zinc oxide, 20 weight % of the dicumyl peroxide, and 40 weight % of the fluorescent red (molecular formula is $C_{24}H_{18}N_2O_2$), and then these materials are mixed together.

A detailed process for producing the component is as follows: the total weight of the thermoplastic elastomer composite is 100 kg. The weight of the agent is 10 Kg. In such case, the agent includes 3 Kg styrene-butadiene-styrene block copolymers, 1 Kg zinc oxide, 2 Kg dicumyl peroxide, and 4 Kg fluorescent red mixed together.

Wherein, 65 Kg thermoplastic elastomer, 25 Kg microspheres foaming agent, and 10 Kg agent are weighed. The mixing ratio of each constituent of the agent is in accordance with the aforementioned mixing ratio. The thermoplastic elastomer, the microspheres foaming agent and the agent are mixed together for 30 minutes. Wherein, the thermoplastic elastomer is purchased from DongBao Plastic Chemical Company Limited, Foshan. The agent is purchased from Ying Quan Chemical Company Limited, Shenzhen. A mould is mounted on a injection moulding machine and the temperature of the mould is adjusted to 40° C. The mould is closed. The mixed thermoplastic elastomer, microspheres foaming agent and agent are injected into the mould. Wherein, the injection pressure is 60 MPa, the injection temperature is 160° C., and the injection speed is 30 cm³/s. The melted materials under the pressure of the pressure maintaining process are solidified for 10 s. After the pressure maintaining process is finished, the product is cooled inside the mould, wherein the duration for cooling is 15 s. Finally, a mould closing device of the injection mould machine controls the moving mould to draw back. The mould is opened and the electronic cigarette component is pushed out, and the whole preparing process is finished.

EXAMPLE 2

A thermoplastic elastomer composite includes 85 weight % of the thermoplastic rubber, 10 weight % of the microspheres foaming agent and 5 weight % of the agent. Wherein, the agent includes 40 weight % of ethylene-vinyl acetate copolymer, 20 weight % of the calcium oxide, 10 weight % of the di-tert-butyl peroxide and 30 weight % of the titanium dioxide, mixed together.

A detailed process for producing the component is as follows: the total weight of the thermoplastic elastomer composite is 100 kg. The weight of the agent is 5 Kg. In such case, the agent includes 2 Kg of ethylene-vinyl acetate copolymer, 1 Kg of the calcium oxide, 0.5 Kg of the di-tert-butyl peroxide and 1.5 Kg of the titanium dioxide, mixed together.

Wherein, 85 Kg thermoplastic rubber, 10 Kg of the microspheres foaming agent and 5 Kg of the agent are weighed. The mixing ratio of each constituent of the agent is in accordance with the aforementioned ratio. The thermoplastic rubber, the microspheres foaming agent and the agent are mixed together for 50 minutes. Wherein, the thermoplastic elastomer is purchased from DongBao Plastic Chemical Company Limited, Foshan. The agent is purchased from Ying Quan Chemical Company Limited, Shenzhen. A mould on a injection moulding machine is mounted, and the temperature of the mould is adjusted to 50° C. The mould is closed. The mixed thermoplastic rubber, microspheres foaming agent and agent are injected into the mould. Wherein, the injection pressure is 50 MPa, the injection temperature is 180° C., the injection speed is 20 cm³/s. The melted materials under the pressure of the pressure maintaining process are solidified for 80 s. After the pressure maintaining process finished, the product is cooled inside the mould, wherein the duration for cooling is 20 s. Finally, a mould closing device of the injection mould machine controls the moving mould to draw back. The mould is opened and the electronic cigarette component is pushed out, and the whole producing process is finished.

EXAMPLE 3

A thermoplastic elastomer composite includes 70 weight % of the thermoplastic polyurethanes, 20 weight % of the microspheres foaming agent and 10 weight % of the agent. Wherein, the agent includes 25 weight % of chlorinated polyethylene, 15 weight % of the stearic acid, 20 weight % of the lauroyl peroxide and 40 weight % of the fluorescein ($C_{20}H_{12}O_5$), and these materials are mixed together.

A detailed process for producing the component is as follows: the total weight of the thermoplastic elastomer composite is 100 kg. The weight of the agent is 10 Kg. In such case, the agent includes 2.5 Kg of chlorinated polyethylene, 1.5 Kg of the stearic acid, 2 Kg of the lauroyl peroxide and 4 Kg of the fluorescein, and then mixed together.

Wherein, 70 Kg of the thermoplastic polyurethanes, 20 Kg of the microspheres foaming agent and 10 Kg of the agent are weighed. The mixing ratio of each constituent of the agent is in accordance with the aforementioned ratio. The thermoplastic polyurethanes, the microspheres foaming agent and the agent are mixed together for 40 minutes. Wherein, the thermoplastic elastomer is purchased from DongBao Plastic Chemical Company Limited, Foshan. The agent is purchased from Ying Quan Chemical Company Limited, Shenzhen. A mould is mounted on a injection moulding machine, and the temperature of the mould is adjusted to 45° C. The mould is closed. The mixed thermoplastic polyurethanes, microspheres foaming agent and agent are injected into the mould. Wherein, the injection pressure is 60 MPa, the injection temperature is 200° C., the injection speed is 40 cm$^3$/s. The melted materials under the pressure of the pressure maintaining process are solidified for 150 s. After the pressure maintaining process finished, the product is cooled inside the mould, wherein the duration for cooling is 17 s. Finally, a mould closing device of the injection mould machine controls the moving mould to draw back. the mould is opened and the electronic cigarette component is pushed out, the whole producing process is finished.

EXAMPLE 4

A thermoplastic elastomer composite includes 75 weight % of a mixture of the thermoplastic elastomer and the thermoplastic rubber, 18 weight % of the microspheres foaming agent and 7 weight % of the agent. Wherein, the agent includes 38 weight % of ethylene-vinyl acetate copolymer, 16 weight % of a mixture of the calcium oxide and zinc carbonate, 15 weight % of the lauroyl peroxide and 31 weight % of permanent yellow G (C34H30N6O6C12), mixed together.

The detailed process for producing the component is as follows: the total weight of the thermoplastic elastomer composite is 100 kg. The weight of the agent is 7 Kg. In such case, the agent includes 2.66 Kg of ethylene-vinyl acetate copolymer, 1.12 Kg of a mixture of the calcium oxide and zinc carbonate, 1.05 Kg of the lauroyl peroxide and 2.17 Kg of permanent yellow G, mixed together.

Wherein, 75 Kg of a mixture of the thermoplastic elastomer and the thermoplastic rubber, 18 Kg of the microspheres foaming agent and 7 Kg of the agent are weighed. The mixing ratio of each constituent of the agent is in accordance with the aforementioned ratio. The mixture of the thermoplastic elastomer and the thermoplastic rubber, the microspheres foaming agent and the agent are mixed together for 35 minutes. Wherein, the thermoplastic elastomer is purchased from DongBao Plastic Chemical Company Limited, Foshan. The agent is purchased from Ying Quan Chemical Company Limited, Shenzhen. A mould is mounted on a injection moulding machine and the temperature of the mould is adjusted to 48° C. The mould is closed. The mixed mixture of the thermoplastic elastomer and the thermoplastic rubber, microspheres foaming agent and agent are injected into the mould. Wherein, the injection pressure is 52 MPa, the injection temperature is 170° C., the injection speed is 25 cm$^3$/s. The melted materials under the pressure of the pressure maintaining process are solidified for 80 s. After the pressure maintaining process finished, the product is cooled inside the mould, wherein the duration for cooling is 18s. Finally, a mould closing device of the injection mould machine controls the moving mould to draw back. The mould is opened and the electronic cigarette component is pushed out, and the whole producing process is finished.

EXAMPLE 5

A thermoplastic elastomer composite includes 78 weight % of the thermoplastic elastomer, 17 weight % of the microspheres foaming agent and 5 weight % of the agent. Wherein, the agent is styrene-butadiene-styrene block copolymers.

A detailed process for producing the component is as follows: the total weight of the thermoplastic elastomer composite is 100 kg. 78 Kg of the thermoplastic elastomer, 17 Kg of the microspheres foaming agent and 5 Kg of the styrene-butadiene-styrene block copolymers are weighed. The thermoplastic elastomer, the microspheres foaming agent and the styrene-butadiene-styrene block copolymers are mixed together for 30 minutes. Wherein, the thermoplastic elastomer is purchased from DongBao Plastic Chemical Company Limited, Foshan. The agent is purchased from Ying Quan Chemical Company Limited, Shenzhen. A mould is mounted on a injection moulding machine and the temperature of the mould is adjusted to 45° C. The mould is closed. The mixed thermoplastic elastomer, microspheres foaming agent and agent are injected into the mould. Wherein, the injection pressure is 56 MPa, the injection temperature is 165° C., the injection speed is 40 cm$^3$/s. The melted materials under the pressure of the pressure maintaining process are solidified for 90 s. After the pressure maintaining process finished, the product is cooled inside the mould, wherein the duration for cooling is 15 s. Finally, a mould closing device of the injection mould machine controls the moving mould to draw back. the mould is opened and the electronic cigarette component is pushed out. The whole producing process is finished.

EXAMPLE 6

A thermoplastic elastomer composite includes 73 weight % of the thermoplastic polyurethanes, 21 weight % of the microspheres foaming agent and 6 weight % of the agent. Wherein, the agent includes 55 weight % of titanium dioxide and 45 weight % of calcium oxide, mixed together.

The detailed process for producing the component is as follows: the total weight of the thermoplastic elastomer composite is 100 kg. The weight of the agent is 6 Kg. In such case, the agent includes 3.3 Kg of titanium dioxide and 2.7 Kg of the calcium oxide, mixed together.

73 Kg of the thermoplastic polyurethanes, 21 Kg of the microspheres foaming agent and 6 Kg of the agent are weighed. The mixing ratio of each constituent of the agent is in accordance with the aforementioned ratio. The thermoplastic polyurethanes, the microspheres foaming agent and the agent are mixed together for 50 minutes. Wherein, the agent is purchased from Ying Quan Chemical Company Limited, Shenzhen. A mould is mounted on a injection moulding machine and the temperature of the mould is adjusted to 48° C. The mould is closed. The mixed thermoplastic polyurethanes, microspheres foaming agent and agent are injected into the mould. Wherein, the injection pressure is 52 MPa, the injection temperature is 185° C., the injection speed is 23 cm3/s. The melted materials under the pressure of the pressure maintaining process are solidified for 100 s. After the pressure maintaining process finished, the product is cooled inside the mould, wherein the duration for cooling is 20 s. Finally, a mould closing device of the injection mould machine controls the moving mould to draw back. The mould is opened and the electronic cigarette component is pushed out, the whole producing process is finished.

EXAMPLE 7

A thermoplastic elastomer composite includes 75 weight % of the thermoplastic rubber, 16 weight % of the microspheres foaming agent and 9 weight % of the agent. Wherein, the agent includes 50 weight % of chlorinated polyethylene, 25 weight % of the stearic acid, and 25 weight % of the lauroyl peroxide, mixed together.

The detailed process for producing the component is as follows: the total weight of the thermoplastic elastomer composite is 100 kg. The weight of the agent is 9 Kg. In such case, the agent includes 4.5 Kg of chlorinated polyethylene, 2.25 Kg of the stearic acid, and 2.25 Kg of the lauroyl peroxide, mixed together.

75 Kg of the thermoplastic rubber, 16 Kg of the microspheres foaming agent and 9 Kg of the agent are weighed. The mixing ratio of each constituent of the agent is in accordance with the aforementioned ratio. The thermoplastic rubber, the microspheres foaming agent and the agent are mixed together for 50 minutes. Wherein, the agent is purchased from Ying Quan Chemical Company Limited, Shenzhen. A mould is mounted on a injection moulding machine and the temperature of the mould is adjusted to 44° C. The mould is closed. The mixed thermoplastic rubber, microspheres foaming agent and agent are injected into the mould. Wherein, the injection pressure is 48 MPa, the injection temperature is 180° C., the injection speed is 23 cm³/s. The melted materials under the pressure of the pressure maintaining process are solidified for 120 s. After the pressure maintaining process finished, the product is cooled inside the mould, wherein the duration for cooling is 20 s. Finally, a mould closing device of the injection mould machine controls the moving mould to draw back. The mould is opened and the electronic cigarette component is pushed out, and the whole producing process is finished.

While the present invention has been described by reference to preferred embodiments, it will be understood by those skilled in the art that various changes may be made and equivalents may be substituted without departing from the scope of the present invention. However, all the changes will be included within the scope of the appended claims.

What is claimed is:

1. A method for producing an electronic cigarette component made of a thermoplastic elastomer composite material, the method comprising the following steps:
    S01: with respect to a total weight of the thermoplastic elastomer composite material, weighing 70-85 weight % of a main body material, 10-25 weight % of a microsphere foaming agent, and 5-10 weight % of an additional agent, and mixing the weighed main body material, microsphere foaming agent, and additional agent together;
    S02: mounting a mould on an injection moulding machine and adjusting a temperature of the mould;
    S03: closing the mould;
    S04: injecting the mixture of the weighed main body material, microsphere foaming agent, and additional agent into the mould at the adjusted temperature, the injecting taking place at an injection speed under a preset injection pressure and at a preset injection temperature, and the injected mixture being molten within the mould;
    S05: solidifying the molten, injected mixture of the main body material, microsphere foaming agent, and additional agent in the mold under a preset maintenance pressure for a predetermined time period and then cooling the solidified mixture of the main body material, microsphere foaming agent, and additional agent together with the mould for a cooling time period so as to form the electronic cigarette component; and
    S06: opening the mould and removing the electronic cigarette component from the mould,
    wherein the electronic cigarette component is at least one of a suction nozzle cover, a protecting sleeve, a crown top, and a suction nozzle, any of which can be provided with decorative patterns similar to tobacco leaves,
    wherein the adjusted temperature of the mould is selected from a range of 40° C. to 50° C.,
    wherein the preset injection pressure is selected from a range 40 Mpa to 60 Mpa and the preset injection temperature is selected from a range of 160° C. to 200° C.,
    wherein the injection speed is selected from a range of 20 cm³/s to 40 cm³/s,
    wherein the predetermined time period is selected from a range of 10 s to 150 s,
    wherein the cooling time period is selected from a range of 15 s to 20 s, and
    wherein the main body material is any one of a thermoplastic polyurethane, a thermoplastic elastomer, and a thermoplastic rubber.

2. The method for producing an electronic cigarette component of claim 1,
    wherein the additional agent comprises 30-40 weight % of a toughener, 10-20 weight % of an activating agent, 10-20 weight % of a cross linking agent, and 30-40 weight % of a toner,
    wherein the toughener is any one of a styrene-butadiene-styrene block copolymers, an ethylene-vinyl acetate copolymer, and a chlorinated polyethylene,
    wherein the activating agent is any one of a calcium oxide, a zinc carbonate, and a stearic acid,
    wherein the cross linking agent is any one of a dicumyl peroxide, a di-tert-butyl peroxide, and a lauroyl peroxide, and
    wherein the toner is any one of a fluorescent red, a titanium dioxide, a fluorescein, and a permanent yellow.

* * * * *